(12) United States Patent
Blackler et al.

(10) Patent No.: US 10,537,576 B2
(45) Date of Patent: Jan. 21, 2020

(54) METHODS FOR TREATING HER2-POSITIVE BREAST CANCER

(71) Applicant: Expression Pathology, Inc., Rockville, MD (US)

(72) Inventors: Adele Blackler, Rockville, MD (US); Todd Hembrough, Gaithersburg, MD (US); Fabiola Cecchi, Rockville, MD (US); Paolo Nuciforo, Barcelona (ES)

(73) Assignee: Expression Pathology, Inc., Rockville, MD (US)

( * ) Notice: Subject to any disclaimer, the term of this patent is extended or adjusted under 35 U.S.C. 154(b) by 0 days.

(21) Appl. No.: 15/374,887

(22) Filed: Dec. 9, 2016

(65) Prior Publication Data

US 2017/0196869 A1 Jul. 13, 2017

Related U.S. Application Data

(60) Provisional application No. 62/265,410, filed on Dec. 9, 2015.

(51) Int. Cl.
*A61K 31/517* (2006.01)
*G01N 33/574* (2006.01)
*G01N 33/68* (2006.01)
*G01N 30/72* (2006.01)
*A61K 39/395* (2006.01)
*A61K 45/06* (2006.01)

(52) U.S. Cl.
CPC ........ *A61K 31/517* (2013.01); *A61K 39/3955* (2013.01); *A61K 45/06* (2013.01); *G01N 33/57415* (2013.01); *G01N 33/6848* (2013.01); *G01N 2333/91205* (2013.01); *G01N 2560/00* (2013.01)

(58) Field of Classification Search
CPC ........... A61K 31/517; G01N 33/57415; G01N 33/6848; G01N 2560/00
See application file for complete search history.

(56) References Cited

U.S. PATENT DOCUMENTS

| 9,765,380 | B2 | 9/2017 | Krizman |
| 2003/0059863 | A1 | 3/2003 | Clinton |
| 2004/0018971 | A1 | 1/2004 | Fikes et al. |
| 2004/0121946 | A9 | 6/2004 | Fikes et al. |
| 2006/0094649 | A1 | 5/2006 | Keogh et al. |
| 2009/0136971 | A1 | 5/2009 | Krizman et al. |
| 2009/0197852 | A9 | 8/2009 | Johnson et al. |
| 2009/0215636 | A1 | 8/2009 | Krizman et al. |
| 2009/0253156 | A1 | 10/2009 | Patton et al. |
| 2010/0021881 | A1 | 1/2010 | Logtenberg et al. |
| 2010/0143927 | A1 | 6/2010 | Sperinde et al. |
| 2010/0299081 | A1 | 11/2010 | Ashman et al. |
| 2013/0122516 | A1 | 5/2013 | Hong et al. |
| 2013/0302328 | A1 | 11/2013 | Krizman |
| 2016/0349259 | A1* | 12/2016 | Bang ...................... C07K 16/32 |
| 2018/0187239 | A1 | 7/2018 | Krizman |

FOREIGN PATENT DOCUMENTS

| EP | 1568373 A2 | 8/2005 |
| EP | 3144394 A1 | 3/2017 |
| WO | 03087831 A2 | 10/2003 |
| WO | 2008/097229 A1 | 8/2008 |
| WO | 2011140464 A2 | 11/2011 |

OTHER PUBLICATIONS

Hembrough et al., J Mol. Diagn.,Jul. 2013, 15(4): 454-465, Epub date: May 11, 2013. (Year: 2013).*
Bartsch et al., Biologics:Targets & Therapy 2007, 1(1): 19-31. (Year: 2007).*
International Search Report as issued in PCT/US2016/065955 dated Mar. 16, 2017.
Lange, V., et al., "Selected reaction monitoring for quantitative proteomics: a tutorial", Molecular Systems Biology, 4 (222):1-14 (2008).
Sano, S., et al., "Absolute Quantitation of Low Abundance Plasma APL1b peptides at Sub-fmol/ml Level by SRm/MRM without Immunoaffinity Enrichment", Journal of Proteome Research, 13:1012-1020 (2014).
Schoenherr, R., et al., "Multiplexed quantification of estrogen receptor and HER2/Neu in tissue and cell lysates by peptide immunoaffinity enrichment mass spectrometry", Proteomics, 12(8):1253-1260 (2012).
Written Opinion as issued in PCT/US2016/065955 dated Mar. 16, 2017.
Sprung, R.W. et al., 'Precision of multiple reaction monitoring mass spectrometry analysis of formalin-fixed, paraffin-embedded tissue'. 2012 Journal of proteome research, 11(6), pp. 3498-3505.
Office Action dated Nov. 14, 2016 issued in Australian Application No. 2011228281, 4 pages.
Office Action dated Jul. 10, 2017 issued in Canadian Application No. 2,820,908, 6 pages.
Office Action dated Jun. 21, 2018 issued in Canadian Application No. 2,820,908, 4 pages.
Office Action and English Translation dated Jun. 5, 2018 issued in Japanese Application No. 2017-175171, 6 pages.
Extended European Search Report dated Mar. 27, 2017 and Jan. 26, 2017 issued in European Application No. 16195288.2, 10 pages.
Office Action dated Feb. 26, 2018 issued in European Application No. 16195288.2, 5 pages.

(Continued)

Primary Examiner — Hong Sang
(74) Attorney, Agent, or Firm — Harness, Dickey and Pierce, P.L.C.

(57) ABSTRACT

Methods of treating breast cancer are provided where a quantitative Her2 assay is used to identify whether a breast tumor will be responsive to treatment with anti-Her2 therapeutic agents such as lapatinib and trastuzumab, followed by selection of a suitable treatment regimen and administration of the regimen. A specific Her2 fragment peptide is precisely quantitated by SRM-mass spectrometry directly in breast tumor cells collected from breast tumor tissue that was obtained from a cancer patient and compared to a reference level in order to determine if the breast cancer patient will positively respond to treatment with a therapeutic agent that specifically targets the Her2 protein.

16 Claims, 3 Drawing Sheets

Specification includes a Sequence Listing.

(56) References Cited

OTHER PUBLICATIONS

Intent to Grant dated Jun. 20, 2018 issued in European Application No. 16195288.2, 6 pages.
Decision to Grant dated Jan. 10, 2019 issued in European Application No. 16195288.2, 2 pages.
Chen et al. Proteomic characterization of Her2/neu-overexpressing breast cancer cells Proteomics 2010, 10, 3800-3810 first published online: Oct. 19, 2010.
International Search Report dated May 25, 2012, issued in the International Application PCT/US2011/064045.
Adam et al: "Comprehensive proteomic analysis of breast cancer cell membranes reveals unique proteins with potential roles in clinical cancer", JBC Papers in Press, XX, XX, Jan. 1, 2002 (Jan. 1, 2002), pp. 1-60.
Fulvia Troise et al: "A novel ErbB2 epitope targeted by human antitumor immunoagents", FEBS Journal, vol. 278, No. 7, Apr. 1, 2011 (Apr. 1, 2011), pp. 1156-1166.
Huang et al., "A high-throughput proteo-genomics method to identify antibody targets associated with malignant disease," Clin. Immunol., (2004) 111:202-209.

* cited by examiner

SEQUENCE LISTING

<160> NUMBER OF SEQ ID NOS: 1

<210> SEQ ID NO 1
<211> LENGTH: 8
<212> TYPE: PRT
<213> ORGANISM: Homo sapiens

<400> SEQUENCE: 1

Glu Leu Val Ser Glu Phe Ser Arg
1               5

METHODS FOR TREATING HER2-POSITIVE BREAST CANCER

This application claims the benefit of U.S. Provisional Application No. 62/265,410 filed Dec. 9, 2015, entitled "Improved methods for treating Her2-positive breast cancer" the contents of which are hereby incorporated by reference in their entirety. This application also contains a sequence listing submitted electronically via EFS-web, which serves as both the paper copy and the computer readable form (CRF) and consists of a file entitled "sequence_listing ST25 TXT", which was created on Mar. 22, 2017, which is 1 KB in size, and which is also incorporated by reference in its entirety.

INTRODUCTION

Improved methods for treating cancer patients are provided by quantitative assay of protein expression in patient tumor tissue, followed by a treatment regimen that is designed and selected based on the results of the assay. The assay provides accurate quantitative levels of Her2 protein expression in the tumor tissue and subsequent analysis of these levels is used to design, select, and administer an optimal treatment regimen for the patient.

In particular, the methods provide an improvement on previous treatment methods by identifying those patients most likely to respond to treatment with the anti-Her2 therapeutic agent lapatinib, also known as Tykerb®, Tyverb®, and lapatinib ditosylate, (referred to herein as lapatinib). The level of Her2 expression in the tumor tissue is determined by quantitating a specified peptide derived from subsequences of the full-length Her2 protein (also referred to as the Neu proto-oncogene, c-ErbB-2, tyrosine kinase-type cell surface receptor HER2, p185erbB2, and CD34), and this level is compared to an absolute reference level. If the level of Her2 expression is lower than the absolute reference level the patient is treated with a regimen that includes a therapeutically effective amount of lapatinib, whereas if the level is above the reference level the patient is treated with a regimen that does not include lapatinib but that may include other anti-Her2 agents including but not limited to trastuzumab (Herceptin®), pertuzumab (Perjeta®), and T-DMI (Kadcyla®). Also provided are methods in which a patient is first treated with a regimen including one or more anti-Her2 agents other than lapatinib, such as trastuzumab, until measured Her2 expression is below the absolute reference level, and then treated with a regimen including lapatinib.

The specified peptide is detected using mass spectrometry-based Selected Reaction Monitoring (SRM), also referred to as Multiple Reaction Monitoring (MRM), and which is referred to herein as an SRM/MRM assay. An SRM/MRM assay is used to detect and quantitatively measure the amount of the specified Her2 fragment peptide, directly in cells procured from cancer patient tissue, such as, for example, formalin fixed cancer tissue. The amount of the peptide is then used to calculate the amount of intact Her2 protein in the tumor sample. Specific and optimized therapeutic agents and treatment strategies can be used to treat an individual cancer patient's disease based on how much of the Her2 protein is present in their cancer cells.

SUMMARY OF THE INVENTION

Methods are provided for treating a patient suffering from breast cancer comprising (a) quantifying the level of a specified Her2 fragment peptide in a protein digest prepared from a tumor sample obtained from the patient and calculating the level of the Her2 peptide in the sample by selected reaction monitoring using mass spectrometry; (b) comparing the level of the Her2 fragment peptide to a reference level, and either (c) treating the patient with a first therapeutic regimen containing an effective amount of the anti-Her2 therapeutic agent lapatinib when the level of the Her2 fragment peptide is lower than the reference level or (d) treating the patient with a second therapeutic regimen that does not contain an effective amount of the antiHer2 therapeutic agent lapatinib when the level of the Her2 fragment peptide is above the reference level. The reference level may be 817 amol/gg, +/−250 amol/gg, +/−150 amol/gg, +/100 amol/gg, +/−50 amol/gg, or +/−25 amol/gg of biological sample protein analyzed. Advantageously, the specified Her2 peptide has the amino acid sequence as set forth as SEQ ID NO: 1. The protein digest of the biological sample may be prepared by the Liquid Tissue® protocol. The protein digest may contain a protease digest, for example a trypsin digest.

In these methods the mass spectrometry method may be, for example, tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry. The mode of mass spectrometry used is may be, for example, Selected Reaction Monitoring (SRM), Multiple Reaction Monitoring (MRM), and/or multiple Selected Reaction Monitoring (mSRM).

The tumor sample may be, for example, a cell, collection of cells, or a solid tissue, for example, formalin fixed solid tissue. The tissue may be paraffin embedded tissue.

In one embodiment, quantifying the specified Her2 fragment peptide comprises determining the amount of the Her2 peptide in the sample by comparing to a spiked internal standard peptide of known amount, where both the native peptide in the biological sample and the internal standard peptide corresponds to the same amino acid sequence of the Her2 fragment peptide as shown in SEQ ID NO:1. The internal standard peptide may be an isotopically labeled peptide, labeled with, for example, one or more heavy stable isotopes selected from $^{18}O$, $^{17}O$, $^{15}N$, $^{13}C$, $^{2}H$ or combinations of these isotopes.

These methods can be combined with detecting and quantitating other peptides from other proteins in a multiplex format so that the treatment decision about which agent used for treatment may be based upon specific levels of the specified Her2 fragment peptide in combination with other peptides/proteins in the biological sample.

In one embodiment, when the level of the specified peptide is higher than the reference level, then the second anti-Her2 therapeutic agent contains trastuzumab, and may optionally contain letrozole, 5-FU (fluorouracil), leucovorin (folinic acid), capecitabine, carboplatin, cisplatin, docetaxel, epirubicin, irinotecan, oxaliplatin, and/or paclitaxel. In another embodiment, when the level of the specified peptide is lower than the reference level, then the first therapeutic regimen further comprises one or more agents selected from the group consisting of letrozole, 5-FU (fluorouracil), leucovorin (folinic acid), capecitabine, carboplatin, cisplatin, docetaxel, epirubicin, irinotecan, oxaliplatin, and paclitaxel.

DETAILED DESCRIPTION

Figure 1:
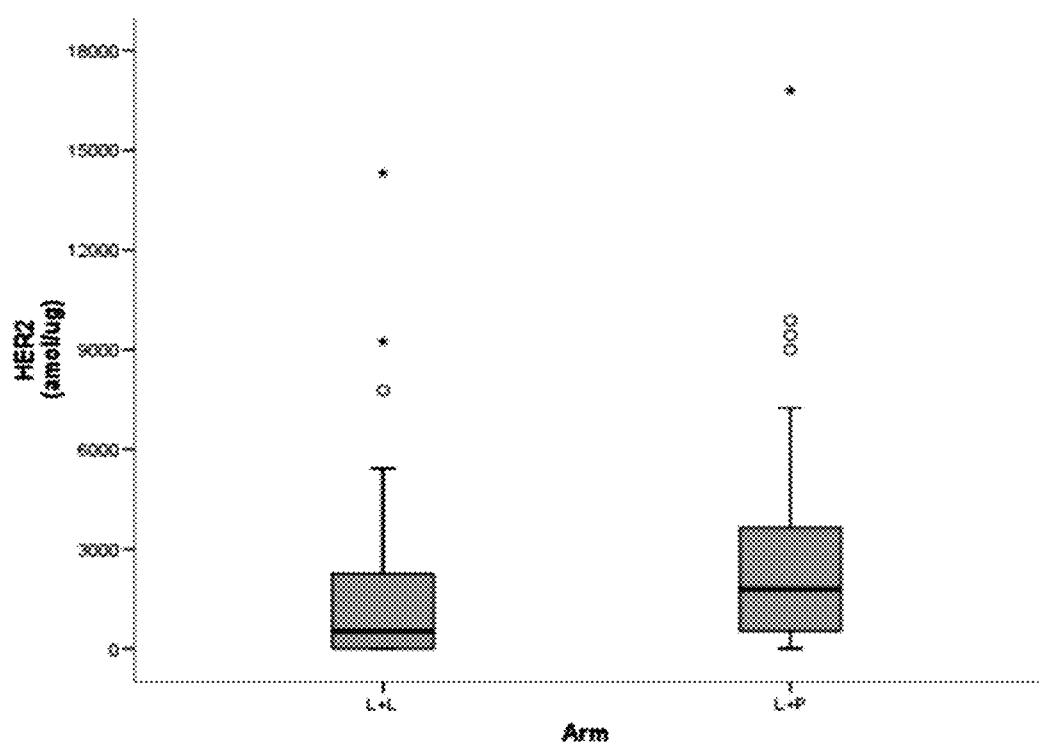
FIG. 1 shows Her2 expression levels as determined by SRM across all samples (see also Table 3). Her2 levels ranged from ND (not detected) to 16,795 amol/μg of protein analyzed. Her2 levels were lower in letrozole+lapatinib (L+L, n=43; mean=1761 amol/μg) compared to letrozole+ placebo (L+P, n=41; mean=2908 amol/μg).

Methods are provided for treating patients suffering from breast cancer. The methods involve testing a sample of tumor tissue from the patient to determine if the patient will clinically respond in a favorable manner to the therapeutic agent lapatinib, and then administering a suitable treatment regimen to the patient. Specifically, methods for measuring absolute amounts of Her2 protein in a tumor sample or samples from a patient are provided, and these methods are used to predict clinical response to lapatinib. The sample is advantageously formalin-fixed and optionally is paraffin embedded. An SRM/MRM assay is provided that measures a specific Her2 peptide fragment, and particular characteristics about this peptide, which is then used to measure the amount of Her2 in cells derived from formalin fixed or formalin fixed paraffin embedded (FFPE) tissue. The peptide fragment uniquely derives from the intracellular domain of the full-length Her2 protein (ICD) and has the sequence ELVSEFSR (SEQ ID NO:1). Surprisingly it has been found that this peptide can be reliably detected and quantitated in digests prepared from FFPE samples of tumor tissue. See U.S. patent application Ser. No. 13/993,045, the contents of which are hereby incorporated by reference in their entirety. Because the peptide is unique to the Her2 protein, one mole of peptide must derive from one mole of Her2 protein and therefore measurement of the molar amount of the peptide provides a measure of the molar amount of the protein.

More specifically, this SRM/MRM assay is used to measure this peptide directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue® reagents and protocol available from Expression Pathology Inc. (Rockville, Md.).

The most widely and advantageously available form of tissue, and cancer tissue, from cancer patients is formalin fixed, paraffin embedded tissue. Formaldehyde/formalin fixation of surgically removed tissue is by far and away the most common method of preserving cancer tissue samples worldwide and is the accepted convention in standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the Her2 protein within the specific cancer of the patient from whom the tissue was collected and preserved. This not only provides diagnostic information about the cancer, but also permits a physician or other medical professional to determine appropriate therapy for the patient. In this case, utilizing this assay provides information about specific levels of Her2 protein expression in cancer tissue and this in turn allows the physician or other medical profession to select and administer a treatment by indicating whether or not the patient from whom the cancer tissue was obtained will respond in a favorable way to therapy with the anti-cancer therapeutic agent lapatinib.

Treating cancer patients with anti-Her2 therapeutic agents such as lapatinib is one of the most common and effective strategies for slowing or stopping tumor growth and thereby prolonging the lives of cancer patients, especially breast cancer patients. The Her2 protein is a signal receptor protein on breast cancer cells and, normally, Her2 receptors help control how a healthy cell grows, divides, and repairs itself. However, in some breast cancers the cancer cells make too many Her2 receptors (Her2 protein overexpression). This makes breast cancer cells grow and divide in an uncontrolled way. In many cases this protein overexpression is accompanied by a Her2 gene that has been amplified, resulting in too many copies of the gene (known as Her2 gene amplification). These extra copies of the Her2 gene can also cause Her2 protein overexpression. It therefore is useful for a clinician to know if a patient's cancer cells express too much Her2 protein because several anti-Her2 therapeutic agents, including lapatinib, are available to treat cancers that are considered Her2 positive. Lapatinib is a tyrosine kinase inhibitor that binds to and inhibits the kinase domain of Her2.

Presently two (2) basic tests are available for determining if a breast cancer patient is a candidate for treatment with anti-Her2 agents, such as trastuzumab or lapatinib. The tests are IHC (immunohistochemistry) and FISH (Fluorescence In Situ Hybridization). Both tests use thin sections of tumor samples from a patient. The IHC test utilizes an antibody to detect the Her2 protein and tries to measure Her2 at the protein level in the cancer cells. The results of the IHC test can be: 0 (negative), 1+ (also negative), 2+ (borderline), or 3+ (positive-Her2 protein overexpression). The FISH (Fluorescence In Situ Hybridization) test works at the nucleic acid level and seeks to measure if there are too many copies of the Her2 gene in the cancer cells. The results of the FISH test can be positive (Her2 gene amplification) or negative (no Her2 gene amplification). Because FISH works at the nucleic acid level and does not measure Her2 protein, it can only be used to infer that Her2 gene amplification results in over-expression of Her2 protein.

Generally, only cancers that test IHC 2+ or 3+ or that are FISH positive are deemed likely to respond to the therapeutic agents that target Her2-positive breast cancers. An IHC 2+ test result is deemed borderline and, if a tumor is scored as IHC 2+, then the tissue is retested with the more precise Her2 FISH test. Neither the IHC nor FISH tests provide quantitative data that are predictive of sensitivity to an anti-HER2 therapeutic agent, such as sensitivity to lapatinib in a HER2 positive population.

Research has shown that some Her2 status test results may be misleading or wrong. This is likely because different testing facilities use different rules for classifying positive and negative Her2 status. Each pathologist running the tests also may use different criteria to decide whether the results are positive or negative. In most cases, this happens when the test results are borderline, meaning that the results are neither strongly Her2-positive nor Her2-negative. In other cases, tissue from one area of a breast cancer can test Her2-positive while tissue from a different area of the cancer tests Her2-negative.

Inaccurate Her2 test results may mean that patients diagnosed with breast cancer do not receive the best possible care or even appropriate care. If all or part of a breast cancer is Her2-positive but test results classify it as Her2-negative, physicians are unlikely to recommend treatment with anti-Her2 therapeutic agents, even though the patient could potentially benefit from those agents. If a breast cancer is Her2-negative but test results classify it as Her2-positive, physicians may recommend treatment with anti-Her2 therapeutic agents, even though the patient is unlikely to derive any clinical benefit and is exposed to the agent's secondary risks. Accordingly, there is great clinical value in the ability to correctly evaluate quantitative levels of the Her2 protein in tumors, especially breast tumors, so that the patient will have the greatest chance of receiving the optimum therapy.

Breast cancers with Her2 gene amplification and/or Her2 protein overexpression are designated Hen-positive in pathology reports. Hen-positive breast cancers tend to grow faster and are more likely to spread and recur compared to Her2-negative breast cancers. However, therapeutic agents are available that specifically bind to and inhibit Her2 protein function and are prescribed when a patient's tumor tests positive for Her2. For example, the most commonly used anti-Her2 agent is Herceptin® (chemical name: trastuzumab), which works by binding to the extracellular domain of Her2 receptors on breast cancer cells and blocking them from receiving growth signals. By blocking these signals, Herceptin® may help to slow or even stop the growth of tumor cells. In addition to blocking Her2 receptors, Herceptin® can also help fight breast cancer by alerting the immune system to destroy cancer cells to which it binds.

Another anti-Her2 therapeutic option for some patients with Her2-positive breast cancer is lapatinib (Tykerb®). As described above, lapatinib works by entering tumor cells and inhibiting Her2 kinase function in the intracellular domain of Her2 where unregulated Her2 kinase activity causes cells to grow and divide abnormally. Lapatinib can be used in combination with other non-Her2 targeted agents such as: (1) capecitabine (Xeloda®), a 5-fluorouracil prodrug used to treat advanced HER2-positive breast cancer that has stopped responding to other forms of chemotherapy such as anthracyclines and taxanes, and to Herceptin®, 2) letrozole (Femara®), an aroma(ase inhibitor that interferes with hormone biosynthesis, used to treat postmenopausal women diagnosed with hormone-receptor-positive/HER2-positive advanced-stage breast cancer. Other anti-Her2 therapeutic agents include but are not limited to pertuzumab (an antibody that inhibits dimerization of Her2 with other Her proteins) and neratinib (a kinase inhibitor that inhibits the kinase activity of Her2 and EGFR).

Detection of the fragment peptide ELVSEFSR (SEQ ID NO: 1). and quantitative measurement of the levels of that peptide are carried out in a mass spectrometer by the SRM/MRM methodology, whereby the SRM/MRM signature chromatographic peak area of each peptide is determined within a complex peptide mixture present in a protein digest such as a Liquid Tissue® lysate (see U.S. Pat. No. 7,473,532, as described above). Quantitative levels of the Her2 protein are then determined by the SRM/MRM methodology whereby the SRM/MRM signature chromatographic peak area of an individual specified peptide from the Her2 protein in a biological sample is compared to the SRM/MRM signature chromatographic peak area of a known amount of a "spiked" internal standard for the specified Her2 fragment peptide. Advantageously, the internal standard is a synthetic version of the same exact Her2 fragment peptide that contains one or more amino acid residues labeled with one or more heavy isotopes. Such isotope labeled internal standards are synthesized so that mass spectrometry analysis generates a predictable and consistent SRM/MRM signature chromatographic peak that is different and distinct from the native Her2 fragment peptide chromatographic signature peak and which can be used as a comparator peak. When the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for the Her2 fragment peptide additional information beyond simply the peptide sequence may be used by the mass spectrometer. That additional information is used to direct and instruct the mass spectrometer, (e.g., a triple quadrupole mass spectrometer) to perform the correct and focused analysis of the specified Her2 fragment peptide. The additional information about target peptides in general, and in particular about the specified Her2 fragment peptide, may include one or more of the mono isotopic mass of each peptide, its precursor charge state, the precursor m/z value, the m/z transition ions, and the ion type of each transition ion. The peptide sequence of this specified Her2 fragment peptide and the necessary additional information as described for this specified Her2 fragment peptide is shown in Table 1.

An SRM/MRM may be effectively performed on a triple quadrupole mass spectrometer, presently considered the most suitable instrument for analyzing a single isolated target peptide within a very complex protein lysate that may consist of hundreds of thousands to millions of individual peptides from all the proteins contained within a cell. The additional information referenced above provides the triple quadrupole mass spectrometer with the correct directives to allow analysis of a single isolated target peptide within the complex protein lysate. The skilled artisan will recognize that, although the triple quadrupole instrument is presently the preferred instrument for SRM/MRM assays, such assays also can be developed and performed on any type of mass spectrometer, including a MALDI, ion trap, ion trap/quadrupole hybrid, or triple quadrupole.

To determine an appropriate reference level for Her2 quantitation, tumor samples are obtained from a cohort of patients suffering from breast cancer. The tumor samples are formalin-fixed using standard methods and the level of Her2 in the samples is measured using the methods as described above. The tissue samples optionally may also be examined using IHC and FISH using methods that are well known in the art.

The patients in the cohort are treated with an anti-Her2 therapeutic agent, such as lapatinib and the response of the patients is measured using methods that are well known in the art, for example by recording the overall survival of the patients at time intervals after treatment, and the response to therapy is correlated to the measured Her2 level for each patient. A reference level is determined using statistical methods that are well known in the art, for example by determining the lowest p value of a log rank test. The reference level provides a quantitative measure of Her2 expression that allows prediction of patient response to therapeutic intervention, and specifically to lapatinib treatment. Surprisingly, as described in more detail below, when Her2 levels and clinical response to lapatinib treatment were correlated, it was found that Her2 levels below the reference level were correlated with a positive response to lapatinib treatment, and levels above the reference level predicted a poor clinical response.

Once a reference level is determined it can be used to identify those patients whose Her2 expression level are below the reference level and who are likely to benefit from including lapatinib in their treatment regimen, together with those patients whose Her2 expression level is sufficiently high that use of an anti-Her2 agent, such as lapatinib, is unlikely to be of therapeutic benefit or is otherwise contraindicated. The skilled artisan will recognize that anti-Her2 agents are used as part of a regimen that utilizes additional drugs or combinations of drugs. Treatment regimens for treating breast cancer are known in the art and drugs that are used can include fluorouracil, Cyramza® (ramucirumab), docetaxel, doxorubiein hydrochloride, Herceptin® (trastuzumab), and mitomycin C. Drug combinations used in breast cancer include FU-LV 10 (fluorouracil plus leucovorin), TPF (docetaxel, cisplatin and fluorouracil) and XELIRI (capecitabine plus irinotecan hydrochloride).

Levels of Her2 in patient samples as determined by the SRM/MRM methodology typically are expressed in amol/µg, although other units can be used. The skilled artisan will recognize that a reference level can be expressed as a range around a central value, for example, +/−250, 150, 100, 50 or 25 amol/µg. In the specific example described in detail below a suitable reference level was found to be 817 amol/µg but the skilled artisan will recognize that levels higher or lower than this can be selected based on clinical results and experience.

Because both nucleic acids and protein can be analyzed from the same Liquid Tissue® biomolecular preparation it is possible to generate additional information about disease diagnosis and drug treatment decisions from the nucleic acids in same sample upon which proteins were analyzed. For example, if the Her2 protein is expressed by certain cells at increased levels when assayed by SRM, the data can provide information about the state of the cells and their potential for uncontrolled growth, potential drug resistance and the development of cancers can be obtained. At the same time, information about the status of the Her2 genes and/or the nucleic acids and proteins they encode (e.g., mRNA molecules and their expression levels or splice variations) can be obtained from nucleic acids present in the same Liquid Tissue® biomolecular preparation and can be assessed simultaneously to the SRM analysis of the Her2 protein. Any gene and/or nucleic acid which is present in the same biomolecular preparation can also be assessed simultaneously with the SRM analysis of the Her2 protein. In one embodiment, information about the Her2 protein and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

Example: Determination of a Predictive Value of Her2 Protein Expression Levels for Lapatinib Sensitivity in Her2 Positive Breast Cancer Patients Patients 84 patients from the lapatinib clinical trial EGF30008 study were identified for Her2 quantitative SRM analysis. All patients with histologically confirmed metastatic breast cancer (MBC) were determined to be estrogen receptor positive (ER+) and Her2 positive (Her2+) by immunohistochemistry (IHC) and/or FISH. 43 patients were treated with letrazole plus lapatinib (L+L). 41 patients were treated with letrazole plus placebo (L+P).

Methods

FFPE tumor tissue was microdissected and solubilized for downstream mass spectrometry analysis using the Liquid Tissue® protocol and reagents as described above. Her2 protein levels were quantitated using selected reaction monitoring mass spectrometry (SRMMS). Progression free survival (PFS) and overall survival (OS) were calculated by Kaplan-Meier and log-rank test. Cox proportional hazard models for PFS and OS were used to generate point estimates of hazard ratios and corresponding 95% confidence intervals.

Results

The clinicopathological patient characteristics for this study are shown in Table 2. Her2 expression levels as determined by SRM across all samples are shown in Table 3 and FIG. 1. Across all samples, Her2 levels ranged from ND (not detected) to 16,795 amol/µg of protein analyzed. Despite the fact that all samples were previously determined to be Her2 positive (2+ and 3+) by standard immunohistochemistry, a number of samples show undetectable levels of Her2 by the highly-sensitive SRM methodology. This is likely due to non-specific background staining as a consequence of the IHC method, leading to SRM-negative samples appearing to be positive by IHC. FIG. 1 shows that Her2 levels are lower in letrozole+lapatinib (L+L, n=43; mean=1761 amol/µg) compared to letrozole+placebo (L+P, n=41; mean=2908 amol/µg), although the difference was non-significant (p=0.106). In addition, no expression of EGFR or Her3 was detected in any of the samples.

Figure 2:
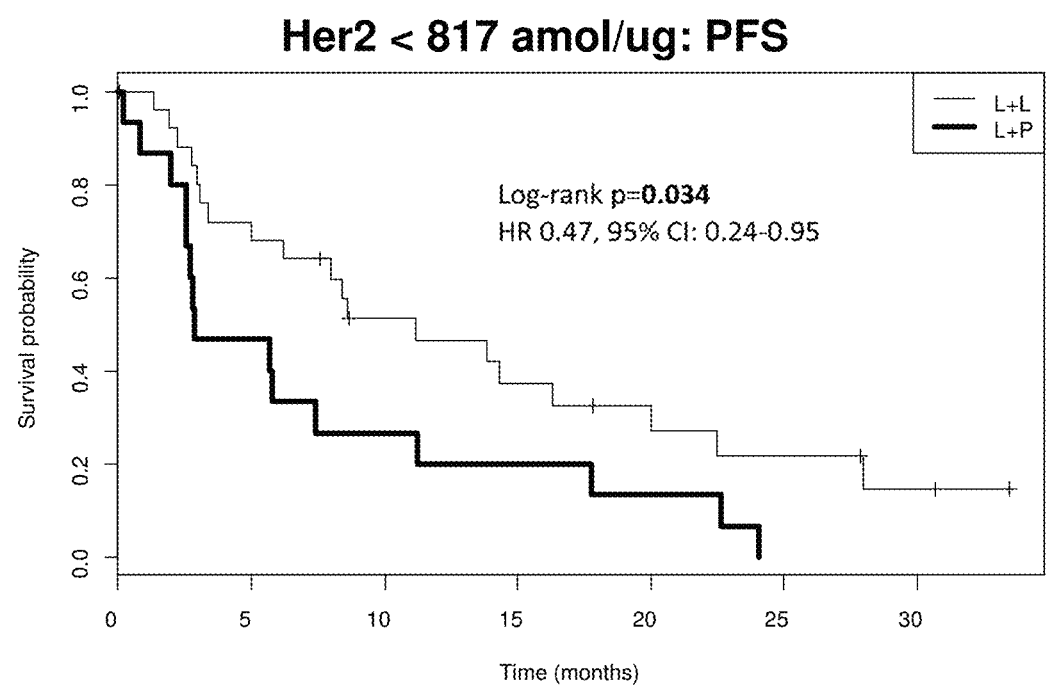
FIG. 2 shows correlation of progression-free survival (PFS). Kaplan-Meier curves show that the combination of letrozole and lapatinib improved the PFS in patients with Her2 levels <817 amol/μg (11.2 vs. 2.9 months, log rank p=0.034).
Figure 3:
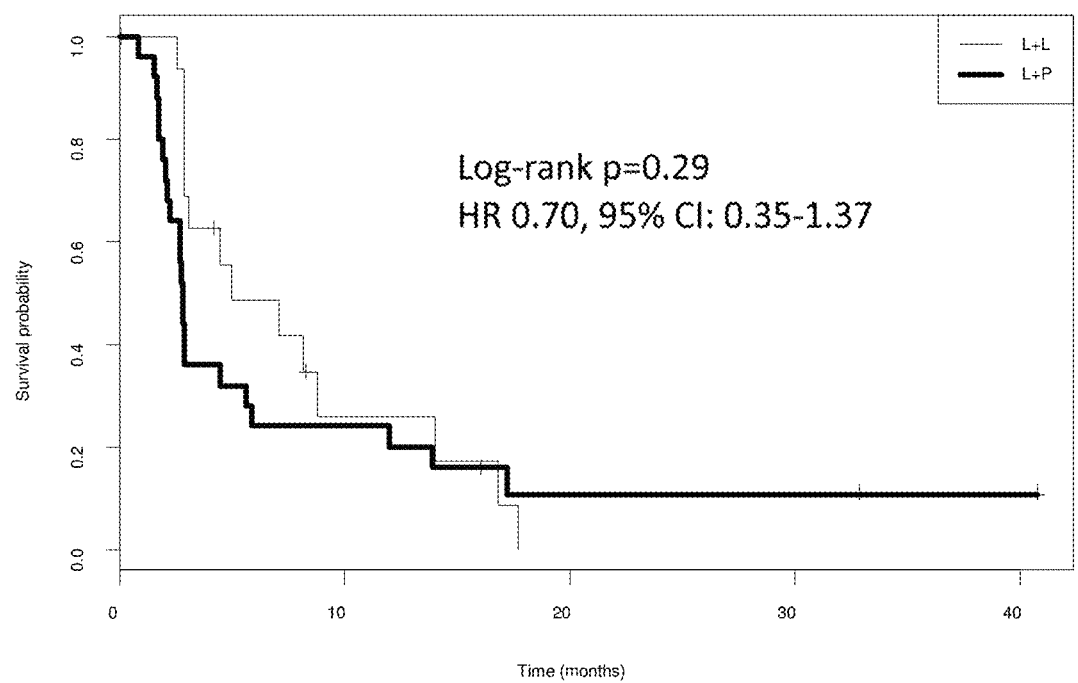
FIG. 3 shows that patients with Her2 levels >817 amol/μg had lower PFS when treated with the combination of letrozole and lapatinib (4.9 vs. 2.8 months, log rank p=0.29).

Her2 SRM results were correlated to progression-free survival (PFS). Kaplan-Meier curves show that the combination of letrozole and lapatinib improved the PFS in patients with Her2 levels <817 amol/µg (FIG. 2; 11.2 vs. 2.9 months, log rank p=0.034) compared to those patients with Her2 levels >817 amol/µg (FIG. 3; 4.9 vs. 2.8 months, log rank p=0.29).

CONCLUSIONS

SRM is a more discriminatory method than IHC to determine whether or not an individual patient will or will not respond to lapatinib. Results indicate the ability to predict treatment outcome from lapatinib whereby those patients whose tumor cells express markedly lower levels of Her2 respond better than those expressing higher levels.

Patients whose tumor cells express <817 amol/µg of protein have a much greater chance of responding to lapatinib than patients whose tumor cells express >817 amol/µg of analyzed protein. Thus, 817 amol/µg protein provides a numerical cutoff for defining treatment with the anti-Her2 drug lapatinib. These presently described results provide a treatment strategy for breast cancer whereby patients whose tumor cells express HER2 at levels below 817 amol/µg are administered a combination regimen of letrozole+lapatinib, while those patients whose tumors express at a level above 817 amol/µg are not treated with this combination but instead are treated with another drug regimen.

Previous data in a different breast cancer patient cohort utilizing this same identical experimental approach correlated Her2-SRM levels to treatment outcome with the anti-Her2 drug trastuzumab. This study demonstrated a cutoff of 2200 amol/µg of protein analyzed whereby patients whose tumor cells express >2200 amol/µg were statistically more likely to respond to a combination treatment regimen that includes the anti-Her2 agent trastuzumab, and whereby patients whose tumor cells express <2200 amol/g of protein were statistically less likely to respond to a combination treatment regimen that included the anti-Her2 agent trastuzumab.

While these two studies cannot be precisely compared due to differences in patient characteristics and therapy regimens administered in different environments, taken together it indicates that a treatment regimen using a drug combination that includes lapatinib should be used in patients expressing lower levels of Her2 (<2200 amol/µg, and particularly <817 amol/µg) whereas a drug combination that includes trastuzumab instead of lapatinib should be used initially in patients with higher Her2 levels (>2200 amol/µg). Additionally, a two-step anti-Her2 therapy can be used where patients are first treated with a drug combination that includes trastuzumab to reduce the number of tumor cells expressing high levels of Her2, followed by treating with a drug combination that includes lapatinib to reduce the remaining cells expressing lower levels of Her2. The first drug combination can be used until Her2 levels fall, for example, to <817 amol/µg, after which the second (lapatinib-containing) regimen is used.

Mass spectrometry-based Her-SRM techniques can objectively measure levels of the Her2 protein directly in FFPE tissue to discern relationships between Her2 levels and clinical outcomes from anti-Her2 therapeutic drugs and drug combinations. A primary result from these studies described above is the delineation of a therapeutic window in which small molecule-based Her2 inhibitors such as lapatinib are better positioned to work than biological Her2 inhibitors such as trastuzumab. Mass spectrometry-based SRM techniques are capable of identifying and grouping cancer patients based on their as Her2 status to identify the most optimal anti-Her2 therapeutic regimen for each patient.

TABLE 1

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | ELVSEFSR | 967.066 | 2 | 483.748 | 538.261 | y4 |
|  |  |  | 2 | 483.748 | 625.294 | y5 |
|  |  |  | 2 | 483.748 | 724.362 | y6 |

TABLE 2

|  | HER2+ SRM population | |
|---|---|---|
|  | N | % |
| N | 84 |  |
| Age (median, range) | 59 (45-87) |  |
| PS |  |  |
| 0 | 41 | 48.81 |
| ≥1 | 43 | 51.19 |
| N° metastatic sites |  |  |
| <3 | 49 | 58.33 |
| ≥3 | 35 | 41.67 |
| Prior adjuvant therapy |  |  |
| <6 months | 33 | 39.29 |
| ≥6 months | 51 | 60.71 |
| Visceral disease |  |  |
| Visceral | 71 | 84.52 |
| Bone | 13 | 15.48 |
| Treatment |  |  |
| L + P | 41 | 48.81 |
| L + L | 43 | 51.19 |

TABLE 3

| HER2 (amol/µg) | ALL | L + L | L + P |
|---|---|---|---|
| N | 84 | 43 | 41 |
| Mean | 2321.1 | 1761.0 | 2908.6 |
| Median | 817.6 | 533.1 | 1790.3 |
| Standard deviation | 3246.8 | 2905.8 | 3509.7 |
| Min | 0.0 | 0.0 | 0.0 |
| Max | 16795.0 | 14301.7 | 16795.0 |

The invention claimed is:

1. A method of treating a patient suffering from breast cancer comprising: administering to the patient a therapeutic regimen comprising an effective amount of lapatinib, wherein a mass spectrometry analysis of a protein digest of a formalin fixed tumor sample from the patient evidences an amount of a HER2 fragment peptide of SEQ ID NO:1 less than or equal to 817±250 amol/μg.

2. The method of claim 1, wherein the amount of the HER2 fragment peptide of SEQ ID NO:1 is less than or equal to 817 amol/μg, ±150 amol/μg.

3. The method of claim 1, wherein the amount of the HER2 fragment peptide of SEQ ID NO:1 is less than or equal to 817 amol/μg, ±100 amol/μg.

4. The method of claim 1, wherein the amount of the HER2 fragment peptide of SEQ ID NO:1 is less than or equal to 817 amol/μg, ±50 amol/μg.

5. The method of claim 1, wherein the amount of the HER2 fragment peptide of SEQ ID NO:1 is less than or equal to 817 amol/μg, ±25 amol/μg.

6. The method of claim 1, wherein the protein digest comprises a protease digest.

7. The method of claim 6, wherein the protein digest comprises a trypsin digest.

8. The method of claim 1, wherein the mass spectrometry comprises tandem mass spectrometry, ion trap mass spectrometry, triple quadrupole mass spectrometry, MALDI-TOF mass spectrometry, MALDI mass spectrometry, hybrid ion trap quadrupole mass spectrometry and/or time of flight mass spectrometry.

9. The method of claim 8, wherein a mode of mass spectrometry used is Selected Reaction Monitoring (SRM), Multiple Reaction Monitoring (MRM), and/or multiple Selected Reaction Monitoring (mSRM).

10. The method of claim 1, wherein the formalin fixed tumor sample is a cell, collection of cells, or a solid tissue.

11. The method of claim 10, wherein the formalin fixed tumor sample is solid tissue.

12. The method of claim 11, wherein the formalin fixed solid tissue is paraffin embedded tissue.

13. The method of claim 1, further comprising detecting and quantifying the Her2 fragment peptide of SEQ ID NO:1 by determining the amount of the Her2 fragment peptide of SEQ ID NO:1 in the sample by comparing to a spiked internal standard peptide of known amount, wherein the internal standard peptide consists of the same amino acid sequence of SEQ ID NO:1.

14. The method of claim 13, wherein the internal standard peptide is an isotopically labeled peptide.

15. The method of claim 14, wherein the isotopically labeled internal standard peptide comprises one or more heavy stable isotopes selected from the group consisting of $^{18}O$, $^{17}O$, $^{15}N$, $^{13}C$, $^{2}H$ and a combination thereof.

16. The method of claim 1, wherein the therapeutic regimen further comprises one or more agents selected from the group consisting of letrozole, 5-FU (fluorouracil), leucovorin (folinic acid), capecitabine, carboplatin, cisplatin, docetaxel, epirubicin, irinotecan, oxaliplatin, and paclitaxel.

* * * * *